United States Patent
Håkansson

[11] Patent Number: 5,988,313
[45] Date of Patent: Nov. 23, 1999

[54] EARPLUG

[75] Inventor: Jörgen Håkansson, Tyringe, Sweden

[73] Assignee: Dalloz Safety AB, Billesholm, Sweden

[21] Appl. No.: 08/989,007

[22] Filed: Dec. 11, 1997

[30] Foreign Application Priority Data

Dec. 12, 1996 [SE] Sweden ................................... 9604578

[51] Int. Cl.$^6$ ....................................................... A61B 7/02
[52] U.S. Cl. ............................................................. 181/135
[58] Field of Search ..................................... 181/129, 130, 181/135; 2/209; 128/864, 865, 867

[56] References Cited

U.S. PATENT DOCUMENTS

| | | | |
|---|---|---|---|
| 1,016,877 | 2/1912 | Elliott . | |
| 2,246,737 | 6/1941 | Knudsen | 181/135 |
| 2,538,339 | 1/1951 | Thomas . | |
| 3,080,011 | 3/1963 | Henderson | 181/135 |
| 3,800,791 | 4/1974 | Visor | 181/135 |
| 4,434,794 | 3/1984 | Leight | 128/867 |
| 4,867,149 | 9/1989 | Falco . | |
| 5,467,784 | 11/1995 | Mobley | 128/867 |
| 5,573,015 | 11/1996 | Williams . | |

FOREIGN PATENT DOCUMENTS

| | | |
|---|---|---|
| 0254366 | 1/1988 | European Pat. Off. . |
| 1559694 | 12/1967 | France . |
| 2808525 | 9/1979 | Germany . |
| 4036361 | 7/1991 | Germany . |
| 90151 | 10/1957 | Norway . |
| WO/07914 | 6/1991 | WIPO . |

*Primary Examiner*—Khanh Dang
*Attorney, Agent, or Firm*—Burns, Doane, Swecker & Mathis, L.L.P.

[57] ABSTRACT

An earplug made of an elastic polymeric material, preferably a thermoplastic elastomeric material, and a method for manufacturing the same. The earplug is multi-material-injection moulded with a core or body part (1) and a sealing part (3), the latter being made of an essentially softer material than the core or body part (1). The material of the sealing part has a Shore A Durometer hardness of preferably between about 2 and about 6.

23 Claims, 4 Drawing Sheets

EARPLUG

FIELD OF THE INVENTION

The present invention relates to earplugs of the type having an elongate core or body part and a sealing part connected therewith, and to the manufacture of such plugs.

BACKGROUND ART

Many different kinds of earplugs of the above-mentioned type have been known for a long time. For a long time, use has been made of a core or body part having the character of a stem, at the front part of which a substantially softer sealing part was attached in some suitable manner.

Recently, earplugs of the type mentioned by way of introduction have been manufactured, completely made of elastic polymeric material of a suitable hardness, the sealing part as a rule comprising transversely protruding flange or collar portions, which extend circumferentially and are adapted to engage sealingly with the wall of the auditory canal. In this context, it has been indicated that the core or body part could be made of a material having a higher hardness than the material of the sealing part, but owing to manufacturing difficulties, use has been made of a single polymeric material for the entire plug. This has necessarily resulted in a compromise between axial rigidity (which should be high in order to facilitate insertion) and radial rigidity (which should be low for good adaptation to the auditory canal with maintained comfort).

OBJECTS OF THE INVENTION

An object of the present invention is to provide an earplug, by means of which the above-mentioned compromise can be obviated.

A further object is to provide an earplug which can be manufactured in different designs with maintained excellent sealing and comfort properties.

One more object is to provide a method that renders it possible to manufacture earplugs of the type at issue in an efficient and economic manner.

SUMMARY OF THE INVENTION

The above-mentioned objects are achieved by an earplug, a method and a use having the distinguishing features as defined in the appended claims.

The invention thus is based on the insight that multimaterial-injection moulding can be utilised to manufacture earplugs with different degrees of hardness of the material of the core or body part and the material of the sealing part. As materials, use is preferably made of elastic polymeric material, especially a thermoplastic elastomeric material, so-called TPE material.

It has surprisingly been found possible to multi-material-injection mould, for the manufacture of earplugs, such materials also having a very low Shore A Durometer hardness of the one material. Thus, the sealing part can be quite easily injection-moulded of a material having a Shore A Durometer hardness of less than about 10, while the core or body part can be injection-moulded of a material having a many times higher hardness, typically a Shore A Durometer hardness of between about 40 and about 80, preferably of between about 50 and about 60.

For the sealing part, it has been found advantageous to have a material hardness Shore A Durometer of between about 2 and about 6, preferably of between about 3 and about 5.

Excellent "physical" binding has been achieved between the main parts of the earplug, that is to say the sealing part obtains the desired good connection with the core or body part through the actual injection moulding. No additional connecting steps are required, although it is, of course, also possible to configuratively perform additional form-fit locking.

The multimaterial-injection moulding in combination with the possibility of selecting different, well-balanced degrees of material hardness for the sealing part and the core or body part, respectively, has been found to afford possibilities of applying the invention to many different plug configurations while maintaining extremely good sealing and comfort properties.

Thanks to very low hardness, the sealing part can adapt to and fill essentially all axial and radial sectional forms of the auditory canal, at the same time as the necessary axial rigidity is available, which has been found to make the insertion of the earplug extremely safe and easy.

Studies have demonstrated that a multimaterial-injection-moulded earplug according to the invention contributes to the user of the earplug spontaneously applying the plug in the ear in a fully correct fashion, i.e. the applied earplug obtains in a natural manner extremely good adaptation to the auditory canal, thereby achieving in a group of users an attenuation effect which is in average essentially improved.

The good connection between the sealing part and the core or body part which is obtained according to the invention besides guarantees that the core or body part is not "pressed through" during insertion (which could hurt the ear) and that the sealing part safely leaves the ear when pulling out the earplug.

The combination of a very soft sealing part and an essentially harder core or body part has been found extremely advantageous when the sealing part comprises laterally or transversely protruding sealing portions, such as flange portions. These are circumferentially of annular configuration and, as a rule, of an increasing diameter from the pointed part of the earplug and backward. These flange portions are comparatively thin to yield good adaptation to the wall of the auditory canal.

In one embodiment according to the invention with a Shore A Durometer hardness of less than about 20, preferably less than about 10, of the flange material it has been found that the protruding portions easily yield or bend in relation to the core or body part. Expressed in a different manner, this means that the core or body part obtains a certain clear axial movability or resilience relative to the sealing portions, which further improves the comfort properties. Moreover, it has been found that said resilience affects the resonance frequency of the earplug. In other words, it becomes possible to control the resonance frequency by the changing of parameters, such as the rigidity of the sealing portions and/or the weight of the core or body part, said parameters directly affecting said resonance frequency. It would be preferable to change said weight, which can be easily achieved, for instance, by insertion of a special material in the core or body part.

In this context it should be pointed out that multimaterial-injection moulding quite simply permits that, for instance, the core or body part is injection-moulded of more than one material and/or that special inserts are arranged therein. Weight-controlling materials and/or materials permitting later detection of the earplug may be involved, such detection being per se known.

It should also be mentioned that the skilled person realises that in connection with multimaterial-injection moulding, it is possible to mould integrally with the core or body part or attach thereto an end of a band, a headband or the like, which is adapted to hold two inventive earplugs together.

When the sealing part according to the invention comprises a number of circumferential, transversely protruding sealing flange portions or the like, especially when these protrude essentially perpendicular to the core or body part, it has been found that there will be a substantially decreased tendency toward wrinkling of the flange portions when inserting the earplug. This means that a considerable problem has been obviated, which problem is frequent in connection with flanged plugs according to prior art technique.

According to the invention, multimaterial-injection moulding suitably takes place in a single multimaterial-injection moulding machine, which can be designed according to per se known principles. It has been found advantageous first to injection mould the core or body part and then the outer sealing part. Use is preferably made of a machine of the type having a rotatable table or mould. As a result, the manufacture will be very rational at the same time as good physical binding is ensured owing to good temperature conditions and a short space of time between the different injection moulding steps.

The invention will be described below by means of exemplifying embodiments and with reference to the accompanying drawings.

DESCRIPTION OF THE EMBODIMENT

Figure 1:
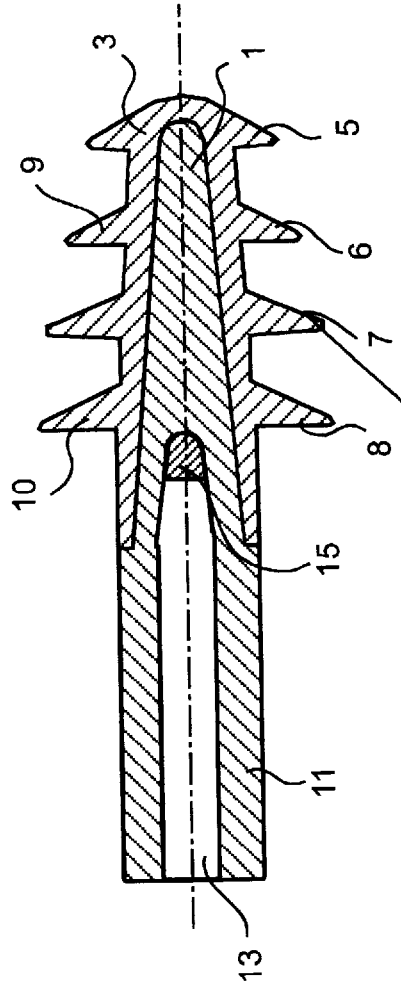
FIG. 1 is a schematic longitudinal section of an embodiment of an earplug according to the present invention.

The earplug shown in FIG. 1 has an essentially conical core or body part 1 which is rounded in the front part and an integrated sealing part physically bound to the circumferential surface of the core or body part by multimaterial-injection moulding. The sealing part 3 has the form of a sleeve closed in the front part, from whose circumferential surface 4 integrated annular flanges 5, 6, 7 and 8 protrude in the radial direction essentially perpendicular to the longitudinal direction of the core or body part. A first flange 5 protrudes directly at the rounded pointed area of the earplug and has the smallest diameter. The other flanges 6, 7 and 8 are uniformly distributed over the actual plug part and have diameters successively increasing backwards along the plug. The front surface 9 of the flanges is inclined backwards while the rear surface 10 of the flanges is perpendicular to the longitudinal or axial direction of the plug.

The sleeve-shaped sealing part 3 covers the entire conical core or body part 1, i.e. the entire actual plug part which is intended to be inserted in the auditory canal of an ear. The core or body part 1 is also extended backwards by a cylindrical grip portion 11, whose diameter is somewhat increased. The grip portion has an axial bore 13, which is adapted to receive a connection part (not shown) of e.g. a band, by means of which a pair of earplugs is kept together in a manner which is per se known. The bore 13 extends with a decreasing diameter a distance into the conical core or body part 1. In the innermost part of the bore, a body 15 is fixedly arranged. The body 15 is suitably made of a magnetic or electrically detectable material, such that a lost plug can be detected in a manner which is per se known. The plug 15 may also comprise a weight, which is used to give the plug the desired resonance frequency, as mentioned in the introductory part of the specification.

The skilled person realises that the body could be replaced by a special core member enclosed in the core or body part 1. Such a core member could also easily be integrated within the scope of the multimaterial-injection moulding.

As an example, the following data for an experimental plug according to FIG. 1 can be stated:

The core or body part 1 is made of a TPE material Cawiton Med PR 3617 B having a Shore A Durometer hardness of about 70.

The sealing part 3 is made of a TPE material Cawiton Med PR 3248 B having a Shore A Durometer hardness of about 4.

The flanges 5–8 have a height of from about 2 to about 4 mm, and a thickness at the base of about 1 mm and approximately half this thickness at the periphery. The outer diameter of the flanges is from about 7 to about 13 mm.

Figure 2:
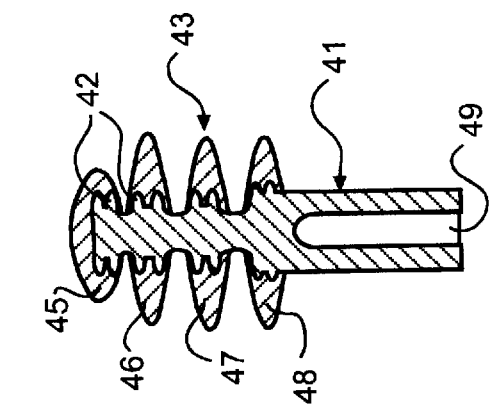
FIGS. 2–4 are similar views of alternative embodiments of an earplug according to the invention.
Figure 3:
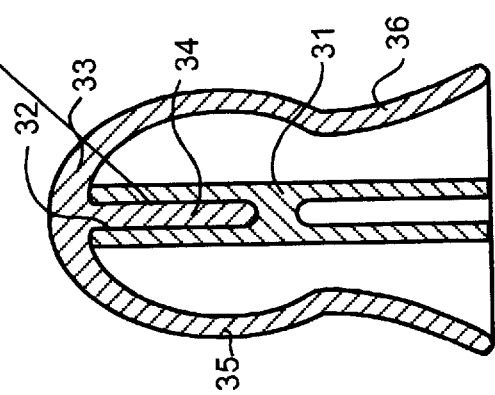
Figure 4:
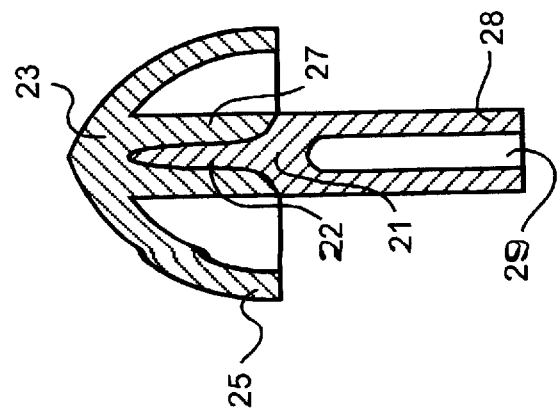

FIGS. 2–4 schematically exemplify a number of alternative embodiments of earplugs according to the present invention. These plugs can be manufactured of the same material as the plug in FIG. 1.

The plug in FIG. 2 has a cylindrical core or body part 21, with whose conically tapering front end part 22 a sealing part 23 is integrated. The actual sealing part comprises a cup-shaped separately projecting part 25 which is swept back. The connection is accomplished by means of a cylindrical pin part 27 which internally projects backwards from the rounded pointed area of the sealing part 23 and which connectingly encloses the end part 22 and has the same diameter as the core or body part 21. This has, like the plug in FIG. 1, a rear grip extension 28 with an axial bore 29 which opens backwards.

The plug in FIG. 3 also has a cylindrical core or body part 31, with whose front end 32 a sealing part 33 is connected via a pin part 34 which internally projects backwards from the pointed area of the sealing part and which is connectingly integrated in a front bore 32 in the core or body part 31. The sealing part 33 has an actual sealing part in the form of an extended, separately projecting part 35 which is swept back from the pointed area over the entire length of the plug. The sleeve-shaped projecting part 35 has a neck 36. The core or body part has also in this case a backwards open, axial bore 39 corresponding to the bores 13 and 29 of the plugs in FIGS. 1 and 2.

The plug in FIG. 4 differs from the plugs in FIGS. 1–3 by the sealing part 43 comprising a number of separate sealing flanges 45, 46, 47, 48 which stand by themselves and which each are integrated with a pin-shaped core or body part 41, whose front part has a number of circumferential grooves 42 for the purpose of improving the binding between the core or body part 41 and the flanges 45–48. Each sealing flange thus fills a groove in a binding manner, and the flange material extends upwards over the two "crests of waves"

adjoining the groove. This results in an enlarged surface in respect of binding and at the same time a certain form-fit locking. The front flange is extended to cover also the pointed part of the plug. It will be appreciated that a possible further development would be to let the materials of the flanges join in the groove or the "trough of the wave" between flanges adjoining each other, in which case fundamentally a basic configuration of the same kind as in FIG. 1 would be obtained, although with an enlarged binding surface. The plug in FIG. 4 is also provided at its back with a bore 49 corresponding to the bores 13, 29, 39 in FIGS. 1–3.

An example of the carrying out of multimaterial-injection moulding of a plug of a basic configuration as shown in FIG. 1 (however without a specific body inserted) will now be described in broad outline with reference to FIGS. 5–7.

Figure 5:
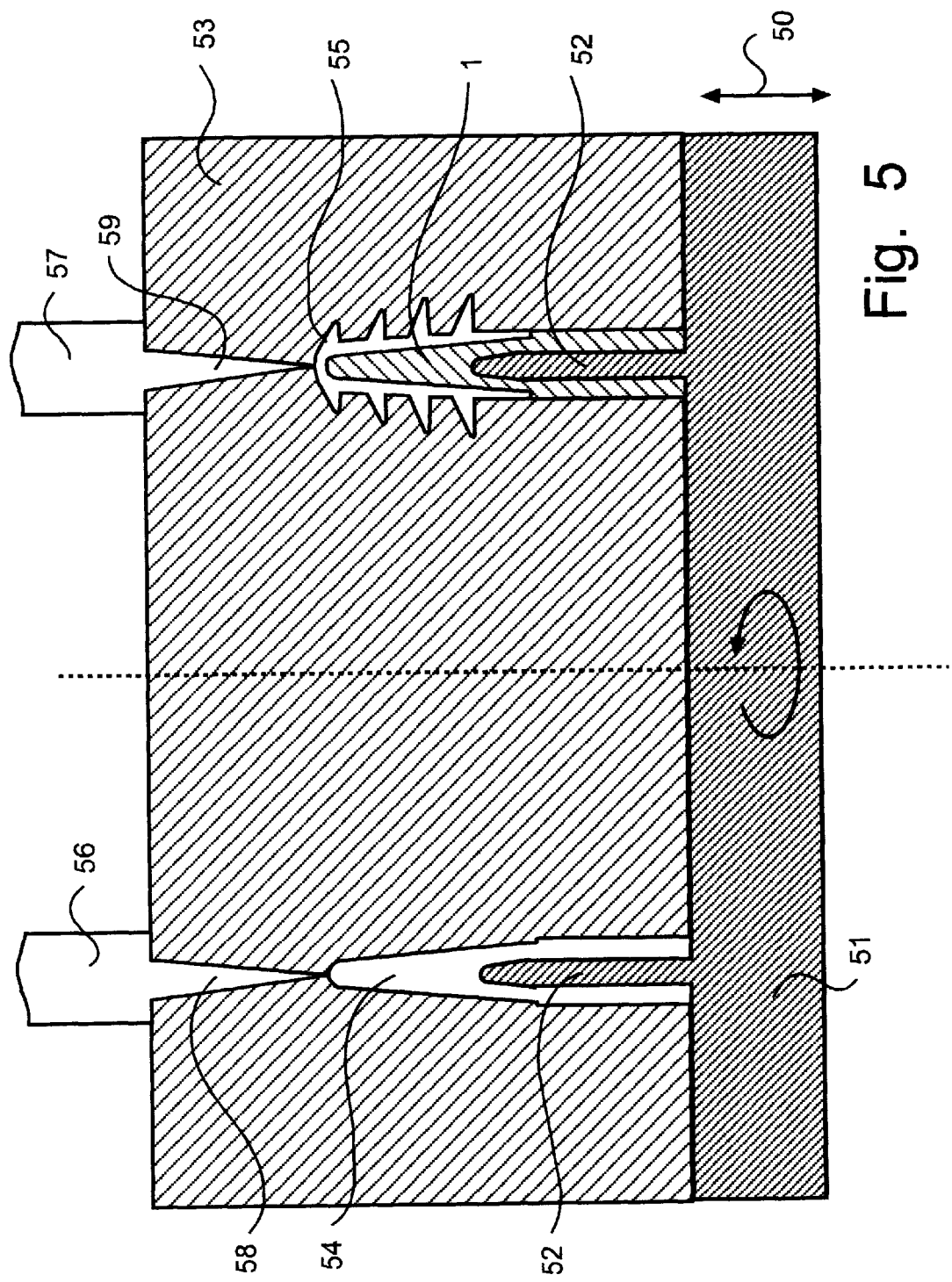
FIG. 5 is a schematic sectional view illustrating, basically, two-material injection moulding in a machine with a rotating table.

FIG. 5 thus illustrates very schematically merely those parts of a multimaterial-injection moulding machine which are relevant to the manufacture of an earplug according to the invention. The other machine parts can be completely conventional and obvious to those skilled in the art.

In FIG. 5, the two halves of the mould of the machine are designated 51 and 53, viz. a rotatable table 51, on which preforming core members 52 are arranged, and a mould half 53 which has cavities 54, 55 and associated injection units 56, 57 with inlet passages 58, 59 to the cavities. Table 51 is movable back and orth relative to mould half 53, as indicated by arrow 50. The preforming core members 52 projecting from the table 51 correspond to the bore 13 in the core or body part of the ear plug. In the moulding position to the left in FIG. 5, the core member 52 projects into a cavity 54 corresponding to the core or body part of the earplug. The cavity 54 is supplied with material from the associated injection unit 56 through the passage 58. In the right-hand moulding position in the figure, a core member 52 with a premoulded core or body part 1 arranged thereon projects into a cavity 55, which corresponds to the finished earplug. The cavity 55 is supplied with material from the associated injection unit 57 through the passage 59.

In the multimaterial-injection moulding, material is injected simultaneously into the cavities 54 and 55, when the halves of the mould 51, 53 have been moved together, as shown in FIG. 5. Subsequently, the mould half 51 is pulled back, such that both the left core member 52 and the core or body part premoulded thereon and the right core member 52, which is pulled out of a ready-moulded plug, will extend freely outside the cavities 54, 55. The mould half 51 is now rotated through 180° at the same time as the ready-moulded plug is removed, after the right part of the mould half 53 has been opened in some suitable manner, which permits the finished plug to be removed.

After removal of the finished plug, the mould half 53 is again closed, whereupon the mould half 51 is moved back into engagement with the mould half 53. The core member 52 which is now arranged to the right and supports the core or body part enters the cavity 55, such that the situation shown in FIG. 1 is again achieved, whereupon the described process is repeated.

Figure 6:
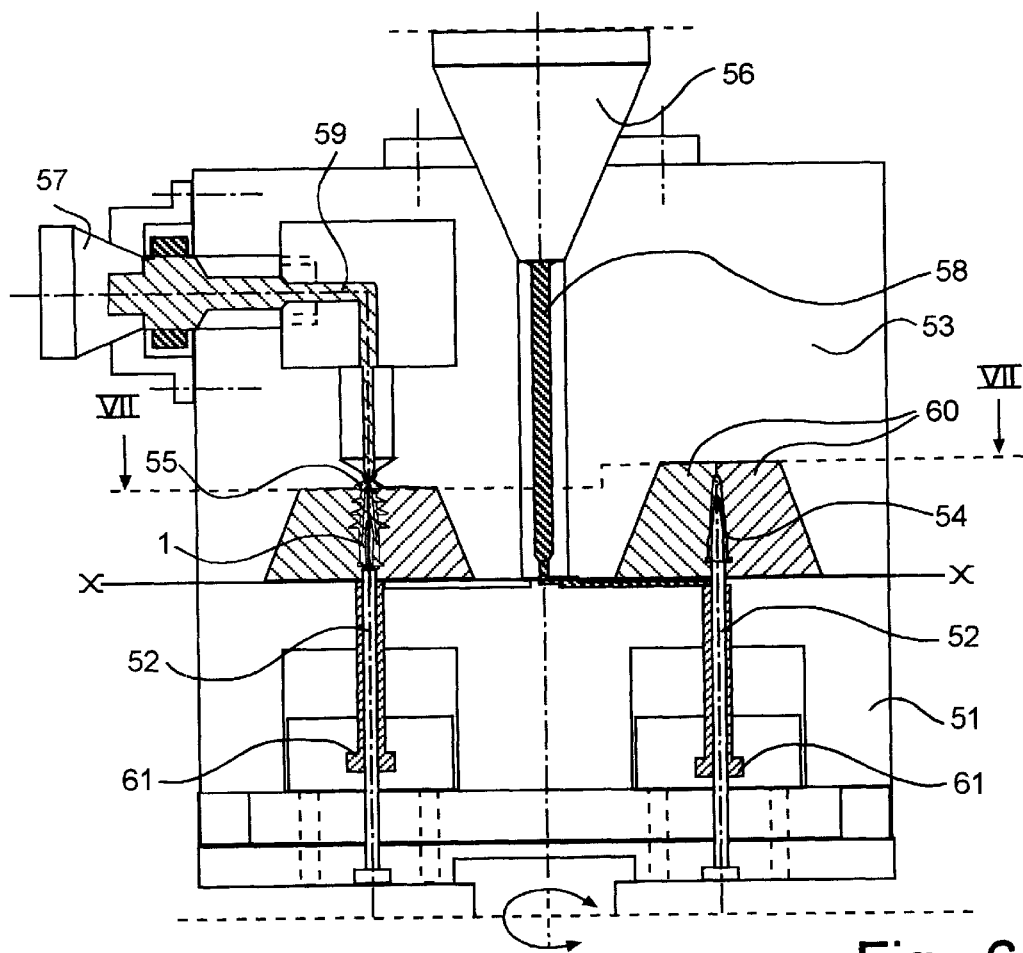
FIG. 6 is a schematic sectional view illustrating an embodiment of a two-material injection moulding device to be used in a moulding machine for manufacturing an earplug according to the invention.
Figure 7:
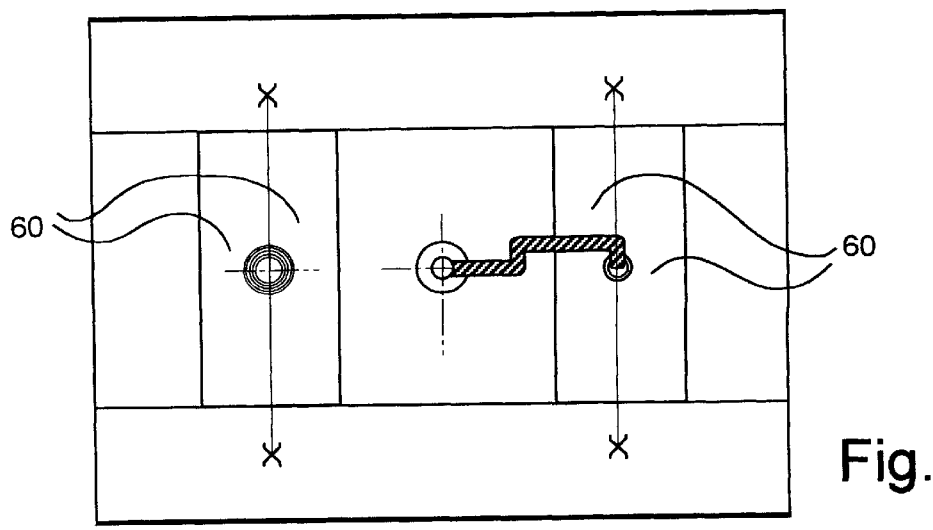
FIG. 7 is a schematic sectional view taken along the line VII—VII in FIG. 6.

FIGS. 6 and 7 illustrate in more detail a preferred embodiment of a mould device operating generally as described with reference to FIG. 5, similar or corresponding elements having the same reference numerals. Additionally, FIGS. 6 and 7 show jaws 60 which define the cavities 54 and 55 and which are movable to the side in order to open the cavities when a finished plug is to be removed. Ejectors 61 are arranged on extensions of the core members 52, the ejectors being displaceable therealong for ejecting a finished earplug after the opening of the associated cavity. Suitably, the mould device can be used in a moulding machine such as FERROMATIK MILACRON, KLÖCKNER 75 ton 2F, 1996. Since the general operation of a multimaterial injection moulding machine is well known to the man skilled in art, no further description thereof should be necessary.

As will be appreciated, the manufacturing process described above implies that the plug will be manufactured in an integrated manner of two materials in two directly successive steps in one and the same machine, which results in great advantages in terms of manufacture while ensuring a good connection between the sealing part and the core or body part.

Figure 8:
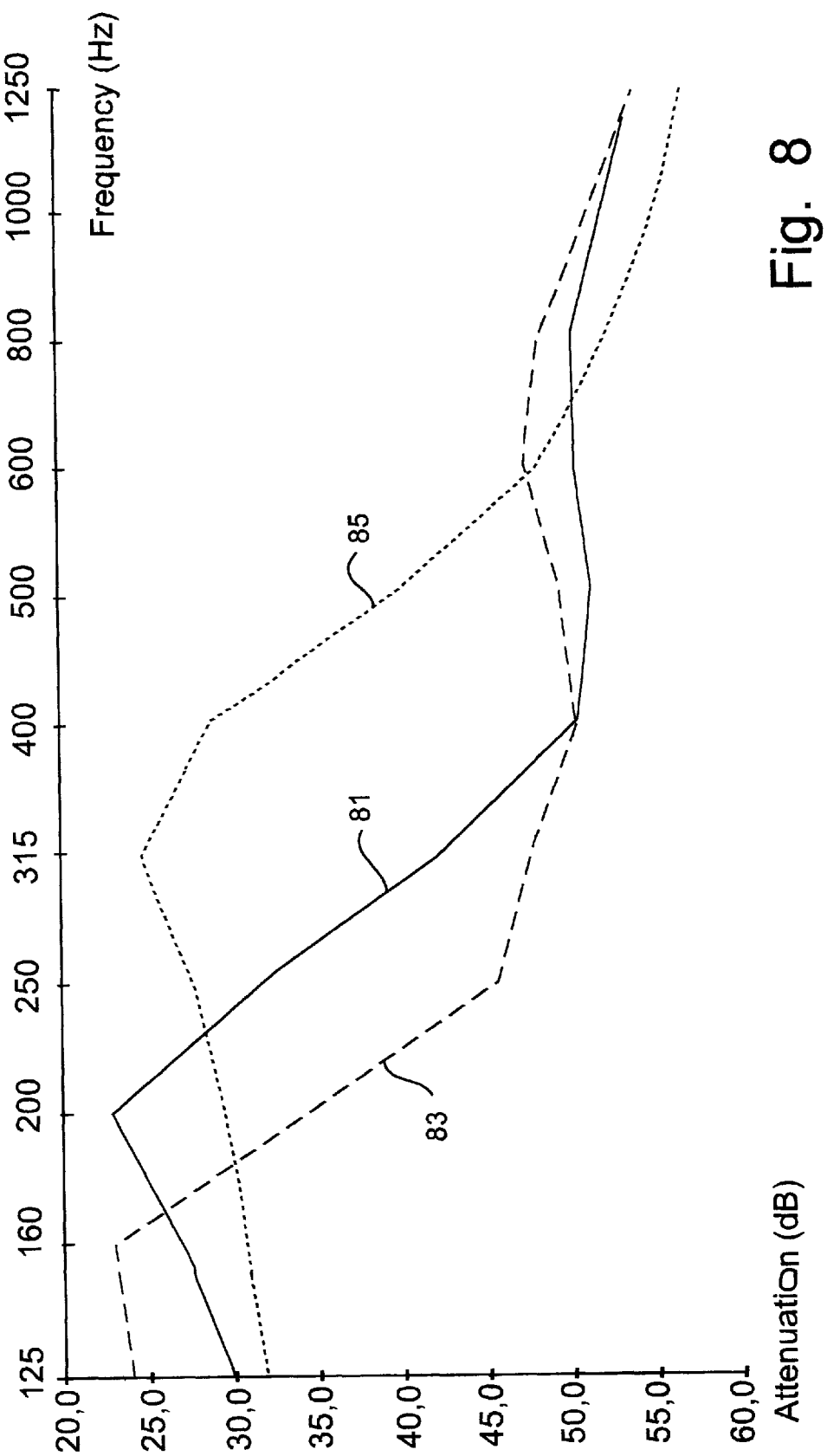
FIG. 8 is a diagram illustrating various attenuation curves obtained when using an earplug according to the invention having various weights of the core or body part.

Also, as previously indicated, the invention makes it possible easily to control the attenuation properties obtained by an earplug as disclosed by selectively changing a certain parameter of the earplug, such as the weight of the core part of the earplug. FIG. 8 illustrates an example thereof. The diagram of this figure shows the attenuation obtained at various frequencies for three earplugs of the type shown in FIG. 1, the weights of the core part of the earplugs being different. Otherwise, the earplugs were identical.

Curve 81 shows the attenuation obtained for an earplug having a reference core part weight of 1.0. Curve 83 shows the attenuation obtained for an earplug having a relative core part weight of 1.6. Curve 85 shows the attenuation obtained for an earplug having a relative core part weight of 0.4. As clearly indicated, the resonance frequency of the earplug will be affected by tye core part weight, while maintaining the same comfort and sealing properties in view of the fact that the sealing portions of the earplug will remain unaffected.

I claim:

1. An earplug of elastic polymer material, comprising an elongate core or body part and a sealing part connected with the core or body part and essentially encompassing the latter at least partially, the material of the sealing part being considerably softer than that of the core or body part, the earplug being multimaterial-injection moulded, and wherein the material of the sealing part has a Shore A Durometer hardness of less than about 10.

2. An earplug as claimed in claim 1, wherein the material of the sealing part has a Shore A Durometer hardness of between about 2 and about 6.

3. An earplug as claimed in claim 1, wherein the material of the core or body part has a Shore A Durometer hardness of between about 40 and about 80.

4. An earplug as claimed in claim 1, wherein the sealing part has the form of a sleeve which is closed at the front end of the plug.

5. An earplug as claimed in claim 1, wherein the sealing part comprises circumferential, transversely protruding flange portions.

6. An earplug as claimed in claim 1, wherein the sealing part comprises a number of separate, circumferential, transversely protruding flange portions.

7. An earplug as claimed in claim 6, wherein the flange portions protrude essentially perpendicular in relation to the elongate core or body part.

8. An earplug as claimed in claim 4, wherein the sleeve-shaped sealing part is, at the front end of the plug, connected with the elongate core or body part and, from there, extends backward along the elongate core or body part at a distance from the latter.

9. An earplug as claimed in claim 8, wherein the sleeve-shaped sealing part has a neck-shaped portion.

10. An earplug as claimed in claim 2, wherein the sealing part has the form of a sleeve which is closed at the front end of the plug.

11. An earplug as claimed in claim 2, wherein the sealing part comprises circumferential, transversely protruding flange portions.

12. An earplug as claimed in claim 2, wherein the sealing part comprises a number of separate, circumferential, transversely protruding flange portions.

13. An earplug as claimed in claim 2, wherein the material of the sealing part has a Shore A Durometer hardness of between about 3 and about 5.

14. An earplug as claimed in claim 3, wherein the material of the core or body part has a Shore A Durometer hardness of between about 50 and about 60.

15. An earplug as claimed in claim 1, wherein the sealing part has the form of a sleeve which is closed at the front end of the plug.

16. An earplug as claimed in claim 1, wherein the sealing part comprises circumferential, transversely protruding flange portions.

17. An earplug as claimed in claim 1, wherein the sealing part comprises a number of separate, circumferential, transversely protruding flange portions.

18. An earplug as claimed in claim 1, wherein the elastic polymer material is a thermoplastic elastomeric material.

19. An earplug of elastic polymeric material, comprising an elongate core or body part and a sealing part connected therewith and comprising a number of circumferential flange portions which project essentially perpendicular in the transverse direction, wherein the sealing part is produced in an integrated manner by means of multimaterial-injection moulding, the material of the sealing part is substantially softer than the material of the core or body part, the height/thickness ratio of the flange portions is selected such that the flange portions have high flexibility relative to the core or body part during axial relative motion of the latter; and wherein the material of the sealing part has a Shore A Durometer hardness of less than about 20.

20. An earplug as claimed in claim 19, wherein the material of the sealing part has a Shore A Durometer hardness of less than about 10.

21. An earplug as claimed in claim 20, wherein the material of the sealing part has a Shore A Durometer hardness of between about 2 and about 6.

22. An earplug as claimed in claim 21, wherein the material of the sealing part has a Shore A Durometer hardness of between about 3 and about 5.

23. An earplug as claimed in claim 19, wherein the elastic polymer material is a thermoplastic elastomeric material.

* * * * *